United States Patent

Weber-Unger et al.

[11] Patent Number: 6,136,028
[45] Date of Patent: Oct. 24, 2000

[54] BREAST PROSTHESIS WORN IN A BRASSIERE OR THE LIKE

[75] Inventors: Georg Weber-Unger, Kufstein, Austria; Stephan Volk, Miesbach, Germany

[73] Assignee: F + E Gesellschaft für Bekleidungsinnovation mbH & Co., KG, Brannenburg, Germany

[21] Appl. No.: 09/193,133

[22] Filed: Nov. 17, 1998

[30] Foreign Application Priority Data

Aug. 24, 1998 [DE] Germany ............ 198 38 428

[51] Int. Cl.⁷ ..................... A61F 2/52
[52] U.S. Cl. ............................ 623/7
[58] Field of Search ............... 623/7, 8, 11, 12

[56] References Cited

U.S. PATENT DOCUMENTS

| | | | |
|---|---|---|---|
| 2,345,649 | 4/1944 | Zimmerman et al. | 623/7 |
| 2,543,499 | 2/1951 | Kausch | 623/7 |
| 3,285,247 | 11/1966 | Morin | 623/7 |
| 3,681,787 | 8/1972 | Perras | 623/7 |
| 3,706,104 | 12/1972 | Dehlin et al. | 623/7 |
| 3,845,507 | 11/1974 | Kirby et al. | 623/7 |
| 3,860,969 | 1/1975 | Arion | 623/8 |
| 3,911,503 | 10/1975 | Hankin . | |
| 4,172,298 | 10/1979 | Rechenberg | 623/7 |
| 4,676,795 | 6/1987 | Grundei . | |
| 5,066,302 | 11/1991 | Rice | 623/7 |
| 5,071,433 | 12/1991 | Naestoft et al. | 623/7 |
| 5,092,881 | 3/1992 | Weber-Unger et al. . | |
| 5,480,429 | 1/1996 | Weber-Unger . | |
| 5,693,164 | 12/1997 | Chang . | |
| 5,738,812 | 4/1998 | Wild . | |
| 5,895,423 | 4/1999 | Becker et al. | 623/8 |

FOREIGN PATENT DOCUMENTS

| | | |
|---|---|---|
| 0 178 483 | 9/1985 | European Pat. Off. . |
| 0 384 951 | 7/1989 | European Pat. Off. . |
| 384 951 | 5/1990 | European Pat. Off. . |
| 0 657 148 | 2/1994 | European Pat. Off. . |
| 824 001 | 2/1998 | European Pat. Off. . |
| 44 13 076 | 4/1994 | Germany . |
| WO 89/05615 | 6/1989 | WIPO . |
| WO 98/26735 | 6/1998 | WIPO . |

*Primary Examiner*—V. Millin
*Assistant Examiner*—Tram A. Nguyen
*Attorney, Agent, or Firm*—Pennie & Edmonds LLP

[57] ABSTRACT

A breast prosthesis worn in a brassiere or the like. It has a prosthesis body having a front side in the shape of a natural breast, a back side with a recess and a prosthesis edge which follows a closed line on which the front side and the back side both end. The prosthesis body has a soft elastic silicone rubber compound which is enclosed without any voids in a bag consisting of two elastically expandable plastic films joined tightly together along the edge of the prosthesis. When the wearer is lying down, the prosthesis should assume a stretched form, where the front side is flattened slightly. When the wearer stands upright, the upper part should sag downward slightly, with the lower and middle areas of the front side having a somewhat greater bulge. This is achieved according to this invention by means of a notch which runs across the longitudinal axis of the wearer's body and is bordered by opposing walls of the upper and lower parts of the prosthesis body and a middle section connecting the lower part flexibly. The middle section permits the upper part to sag relative to the lower part under the influence of gravity, and sagging of the upper part causes an elastic bending deformation of the middle section and is limited by the opposing walls of the notch coming in contact.

8 Claims, 2 Drawing Sheets

BREAST PROSTHESIS WORN IN A BRASSIERE OR THE LIKE

BACKGROUND OF THE INVENTION

The present invention concerns a breast prosthesis to be worn in a brassiere or the like, with a prosthesis body which has a front side having the shape of a natural breast, a back side provided with a recess and an edge of the prosthesis which follows a closed line, along which the front side and the back side of the prosthesis body each end, and the prosthesis body has a soft elastic silicone rubber compound enclosed without any voids in a bag consisting of two elastically expandable plastic films bonded tightly together along the edge of the prosthesis.

Such a breast prosthesis was presented and described in European Patent No. 657,148 A1, for example. With this breast prosthesis, one or more reinforcing ribs run vertically in the upright position of the prosthesis wearer and parallel to the longitudinal axis of the wearer's body; the function of these reinforcing ribs is to prevent the prosthesis body from sagging under the influence of gravity when the prosthesis wearer is in an upright position. In other words, the reinforcing ribs should guarantee the dimensional stability of the prosthesis when the wearer is in an upright position. However, the reinforcing ribs of the known breast prosthesis also have the effect of maintaining the shape of the prosthesis body even when the prosthesis wearer is lying down, because they prevent the prosthesis body from stretching horizontally under the influence of gravity when the prosthesis wearer is lying down. Many prosthesis wearers perceive it as unnatural when the prosthesis has the same shape when the wearer is lying down as when standing. To put it more explicitly, these prosthesis wearers have complained that this prosthesis does not flatten out somewhat when lying down in comparison with standing up in accordance with the natural conditions. Especially if very soft breast tissue is to be replaced with the prosthesis, as is often the case with older patients, it is perceived as a disadvantage that the prosthesis projects away from the wearer's body with an unnatural stiffness when lying down.

SUMMARY OF THE INVENTION

Therefore, the object of the present invention is to improve on a breast prosthesis worn in a brassiere or the like, with a prosthesis body having a front side with the shape of a natural breast, a back side with a recess and a prosthesis edge which follows a closed line on which each of the front side and the back side end. The prosthesis body has a soft elastic silicone rubber compound which is enclosed without any voids in a bag consisting of elastically expandable plastic films joined tightly together along the edge of the prosthesis. The prosthesis body being characterized in that the recess has at least one elongated notch running across the longitudinal axis of the wearer's body, bordered by opposing walls of an upper part and a lower part of the prosthesis body and a middle section which flexibly connects the upper and lower parts, making it possible for the upper part to sag under the influence of gravity relative to the lower part when the wearer is in an upright position. The sagging of the upper part causes an elastic bending deformation of the middle section and the upper part is limited by contact of at least one part of the opposing walls of at least one elongated notch such that it will change its shape when the wearer changes from a lying position to an upright position, so that the shape of the breast prosthesis corresponds to the natural breast shape even when the wearer of the prosthesis is lying down.

The object of the present invention is achieved by a breast prosthesis having a recess with at least one notch running across the longitudinal axis of the wearer's body, bordered by the opposing walls of an upper and a lower part of the prosthesis body and a middle section connecting the upper part to the lower part, permitting the upper part to sag in a controlled manner relative to the lower part under the influence of gravity when the wearer is in an upright position, where the controlled sagging of the upper part causes an elastic bending deformation of the middle section and is limited by coming in contact with at least one part of the opposing walls of the notch.

The prosthesis according to this invention assumes a relatively flat, extended shape when the prosthesis wearer is lying down. When the wearer stands up, the upper part of the prosthesis body sags under the influence of gravity to the extent that at least part of the opposing walls of the notch come together. The bending deformation of the middle section of the prosthesis body due to the sagging of the upper part of the prosthesis body and the pressure of the walls of the notch contacting against one another result in an increased bulging of the front side in the lower to middle area of the prosthesis body. The prosthesis then has a shape corresponding to the shape of a natural breast of very soft breast tissue. With this shape, the prosthesis fills out the cup of the brassiere very well, so that the prosthesis is optimally adapted to the shape of the cup of a given brassiere in which it is accommodated. The flexible connection between the upper and lower parts of the prosthesis body also leads to an excellent vibrational behavior of the prosthesis which again corresponds to the vibrational behavior of a natural breast of very soft tissue. The alternate stretching and sagging of the prosthesis not only presents a natural vibrational behavior when the wearer is running but also promotes the ventilation and aeration of the back side of the prosthesis, because the alternate widening of the notch and closing of the opposing walls against one another results in an alternate suction intake and pumping of air between the back side of the prosthesis and the body of the wearer. If the wearer is lying down, the prosthesis stretches in a horizontal direction parallel to the longitudinal axis of the wearer's body, with this stretching being induced by the inherent weight of the prosthesis, which is then acting perpendicular to the body of the wearer, and by the restoring force created by the deformation of the middle section. One result of this stretching of the prosthesis when the wearer is lying down is a flattening of the prosthesis, so that now, even when the wearer is lying down, the shape of the prosthesis is adapted to the shape of a natural breast consisting of very soft breast tissue. The middle flexible section, connecting the upper part of the prosthesis body with the lower part of the prosthesis body, can be compared with a film hinge which permits the notch to open and close when the wearer changes between a lying position and an upright position or moves away rapidly. The prosthesis according to this invention is also characterized by a low weight, so the prosthesis is extremely comfortable to wear.

According to a refinement of the present invention, the notch may have a curved shape in the undeformed state instead of following a straight line; this curved shape forces the opposing walls of the notch to remain in contact when the upper part sags in the longitudinal direction of the notch. This counteracts the sagging of the upper part of the prosthesis body to a greater extent than would be the case with a prosthesis where the notch follows a straight line. If the middle section of the prosthesis body is compared with a hinge, the hinge has a self-limiting effect due to the curved shape of the notch. The ability of the prosthesis to change its shape can be influenced to a great extent by having the shape of the notch differ from a straight line, and thus it can be adapted to the individual needs of the prosthesis wearer.

The length of the notch also has an influence on the ability of the prosthesis to change its shape. It has proven especially advantageous if the notch ends a distance away from the edge of the prosthesis, as seen in the longitudinal direction. With such a length of the notch, the lateral portions of the prosthesis are prevented from bending too much when the prosthesis sags.

The ability of the prosthesis to change its shape can also be controlled by the number of transverse notches. For example, the recess may have more than one notch running across the longitudinal axis of the wearer's body, arranged so they are spaced one above the other, based on the longitudinal axis of the wearer's body. Such a prosthesis then results in a series of several hinges, all of which allow an elastic bending deformation of the prosthesis body due to the influence of gravity when the wearer is lying down and upright. The overall bending deformation is distributed to more than one hinge in such a case.

The ability of the prosthesis to adapt to the shape of the natural breast when the wearer is lying and upright is further improved by the fact that the silicone rubber compound is adjusted to a softness with a penetration between 150 and 230. The silicone rubber compound preferably consists of two addition crosslinked components whose viscosity is in the range between 500 and 2500 mPa·s.

The back of the prosthesis body can be covered by a piece of fabric attached to the edge of the prosthesis. This piece of fabric reduces the friction between the prosthesis and the wearer's body, so that it is possible to accelerate the sagging and stretching movements of the prosthesis.

BRIEF DESCRIPTION OF THE DRAWINGS

Two embodiments of the present invention are presented in the drawings and explained in greater detail below. The figures show.

DETAILED DESCRIPTION OF THE INVENTION

Figure 2:
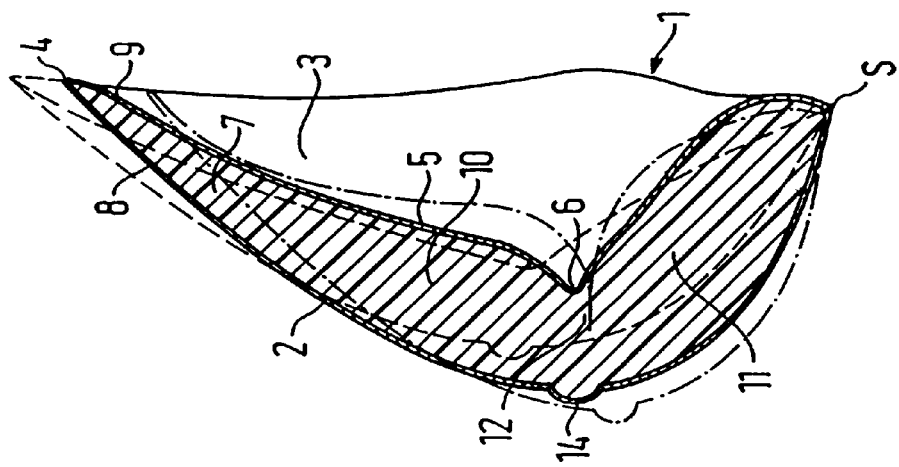
FIG. 2 a cross section through the breast prosthesis illustrated in FIG. 1 along line II—II in FIG. 1, as seen in the direction of the arrows, with the contour of the prosthesis when the wearer of the prosthesis is lying down and standing up also being indicated.
Figure 1:
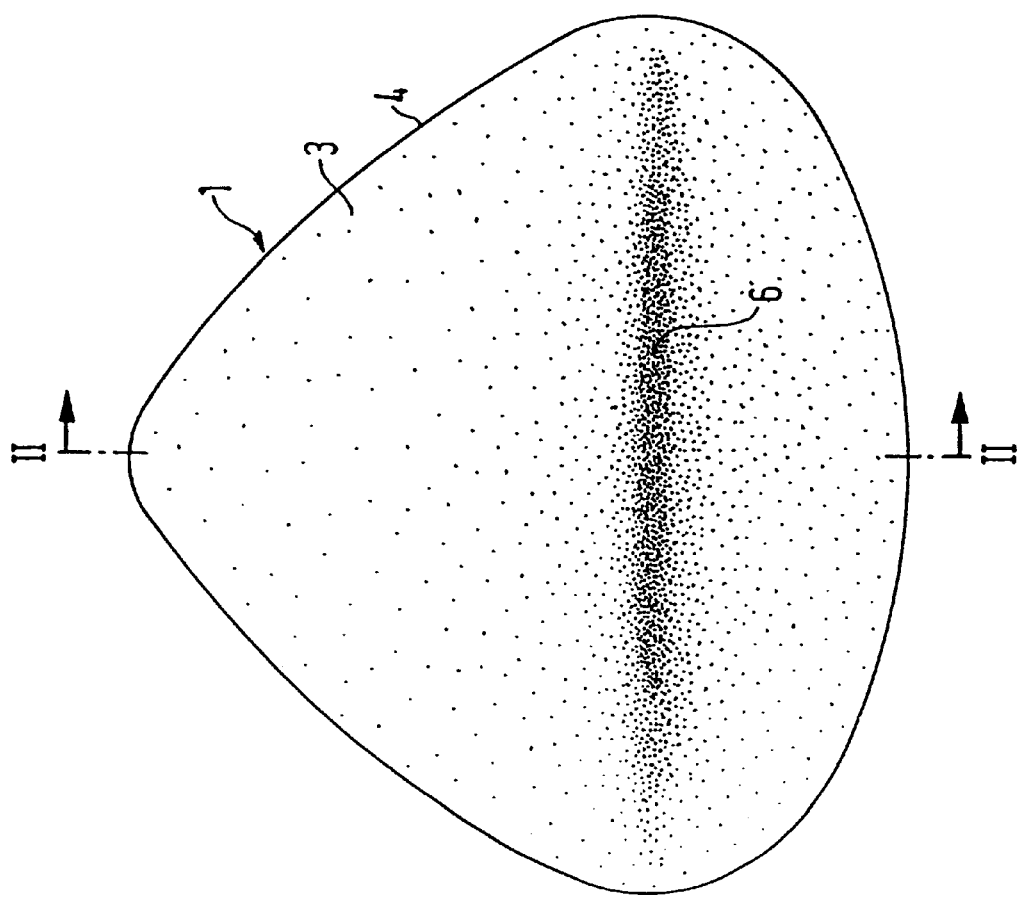
FIG. 1 a top view of the back of a breast prosthesis according to a first embodiment in the undeformed state of the prosthesis.

As shown in FIGS. 1 and 2, the breast prosthesis according to a first embodiment has a prosthesis body 1 having a front side 2, a back side 3 and a prosthesis edge 4 which follows a straight line along which the front side 2 and back side 3 each end. The front side 2 of the prosthesis body 1 has a shape corresponding to that of a natural breast. As explained in greater detail below, the shape of the prosthesis can change between a stretched shape and a sagging state, depending on the position of the prosthesis wearer (lying or upright). The prosthesis is worn in the cup of a brassiere. It is also suitable for being worn in the top part of a bathing suit or bikini. The stretched shape illustrated with dotted lines in FIG. 2 is assumed by the prosthesis when the wearer is lying down. When the wearer is upright, the prosthesis sags, as indicated with a dash-dot line in FIG. 2. When in the stretched shape and in the sagging shape, the shape of the front side 2 corresponds to the shape of a natural breast. The cross-sectional diagram of the prosthesis in FIG. 2 shows the prosthesis in the undeformed state.

The back side 3 of the prosthesis has a recess 5 which according to this invention has a notch 6 running across the longitudinal axis of the wearer's body. The longitudinal axis of the wearer's body runs parallel to sectional line II shown in FIG. 1.

A nub simulating a nipple 14 is provided on the front side 2 of the prosthesis.

The prosthesis body 1 is composed of a soft elastic silicone rubber compound 7 and a bag consisting of two elastically expandable plastic films 8, 9 welded tightly together along the prosthesis edge 4, with the silicone rubber compound 7 enclosed in the bag without any voids. The two plastic films 8, 9 are preferably polyurethane films.

The notch 6 is bordered by the opposing walls of an upper prosthesis body part 10 and a lower prosthesis body part 11 and a middle section 12, flexibly connecting the upper part 10 and the lower part 11 of the prosthesis body 1 to one another.

If the prosthesis wearer changes position from lying to upright, the prosthesis changes its shape from the stretched shape illustrated with a dotted line in FIG. 2 to the sagging shape illustrated with dash-dot lines in FIG. 2. To put it more precisely, when the wearer changes positions from lying down to upright, the upper part 10 sags down in the cup of the brassiere under the influence of gravity, with the sagging of the upper part 10 causing an elastic bending deformation of the middle section 12. The sagging movement of the upper part 10 is stopped when the opposing walls of notch 6 come in contact, so that notch 6 is closed in the longitudinal direction and largely also in the direction of depth. In FIG. 1, which shows the back side 3 of the prosthesis, the notch is represented by a multitude of dots.

As shown in FIG. 2, the sagging of the upper part 10 of the prosthesis body 1 causes the middle area, including nipple 14, and the area of the front side 2 of the prosthesis body below the nipple 14 undergoes a great bulging in comparison with the stretched shape shown with a dotted line; this is associated with a shifting of the nipple 14 forward and downward, with the prosthesis edge 4 being fixed at point S on the wearer's body in the lower area due to the edge of the cup of the brassier. In the sagging condition, the middle area of the front side 2 of the prosthesis body is farther away from the wearer's body than in the stretched position of the prosthesis. The prosthesis edge in the upper area of the front side 2 of the prosthesis body 1 is lower in the sagging condition of the prosthesis than in the stretched position of the prosthesis.

If the wearer changes from an upright position to a lying position, the prosthesis changes its shape by stretching as indicated in FIG. 2. Under the influence of gravity, which is now acting on the prosthesis from a direction that has changed by 90°, the upper part 10 of the prosthesis body moves back upward, while notch 6 assumes a shape as illustrated with a dash dot line in FIG. 2. Stretching of the prosthesis is supported by the resiliency of the elastically deformed middle section 12. As a result of the stretching, of the prosthesis, the front side 2 flattens out again, and the curvature of the front side decreases in the middle and lower areas. The lowest point of the prosthesis is in the lowest area of prosthesis edge 4 in the stretched position. The movement of the prosthesis from the stretched shape to the sagging shape (and back again) can also be described as a rolling movement about the point S.

Notch 6 ends at a distance from prosthesis edge 4, as shown in FIG. 1, in the first embodiment illustrated here.

If the wearer is in an upright position and if the prosthesis is exposed to a dynamic load, e.g., in running, the prosthesis changes its shape alternately between the shapes illustrated with dotted lines and with dash-dot lines in FIG. 2. This change in shape under dynamic stress corresponds largely to the vibrational behavior of the natural breast under dynamic stress.

The alternate stretching and sagging of the prosthesis promote the ventilation and aeration of the back side of the prosthesis, because air is drawn in and pumped out by the alternate opening and closing of the notch 6. Good ventilation and aeration of the prostheses prevents any unpleasant buildup of perspiration on the skin under the prosthesis.

In the example according to FIGS. 1 and 2 as illustrated here, the prosthesis according to this invention is a symmetrical prosthesis, i.e., it can be used on either side. However, the design of the prosthesis according to this invention can also be applied to an asymmetrical prosthesis which can be worn on either the right or the left side. A piece of fabric which reduces the irritation between the prosthesis body and the skin of the prosthesis wearer is applied to the back of the prosthesis. This increases the adaptability of the prosthesis to the shape of the natural breast when the wearer is lying down and standing up.

The silicone rubber compound of the prosthesis according to the present invention has a very soft, sluggish nature. This is achieved by the fact that the silicone rubber compound consists of an addition crosslinked two-component silicone system of $\alpha,\omega$-dimethylpolydimethylsiloxanes, $\alpha,\omega$-divinylpolydimethylsiloxanes with an Si-vinyl content between 0.01 mmol/g and 0.2 mmol/g. SiH-functional polydimethylsiloxanes with an SiH content of 2 mmol/g to 5 mmol/g and platinum complex compounds as catalysts. The viscosity of the two components is between 500 and 2500 mPa.s. The softness of the two-component silicone system is adjusted so that the penetration is between 150 and 230·$\frac{1}{10}$ mm, where the measurement is performed according to DIN 51,580 with a test cone weight of 14.9 g and a cone guide rod weight of 10 g.

The elastic bending deformability of the prosthesis in the area of notch 6 is supported by the very soft nature of the silicone rubber compound.

The second embodiment is very similar to the first embodiment with regard to the composition of the prosthesis and the shape of the front side of the prosthesis in the undeformed state. The only difference between the two embodiments is the shape of the notch, which in the second embodiment leads to the result that the lower area of the front side of the prosthesis bulges out even more in the sagging state, with this bulging being concentrated even more greatly on the center of the front side of the prosthesis and consequently it imparts a pronounced conical shape to the front side of the breast prosthesis.

Because of the extensive correspondence between the two embodiments, the following description is limited to an explanation of the shape of the notch and its effects on the shape of the front side of the prosthesis. The same reference numbers as in the first embodiment are used here, adding only a prime symbol after the respective number. In addition, the only parts labeled are those to which reference must be made to facilitate an understanding of the difference between the two embodiments.

Figure 4:
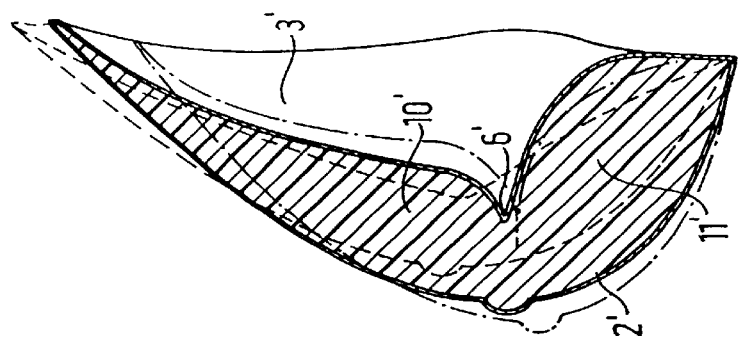
FIG. 4 a cross section of the breast prosthesis shown in FIG. 3 along line IV—IV in FIG. 3 as seen in the direction of the arrows, with the contour of the prosthesis also being indicated when the prosthesis wearer is lying down and standing up.
Figure 3:
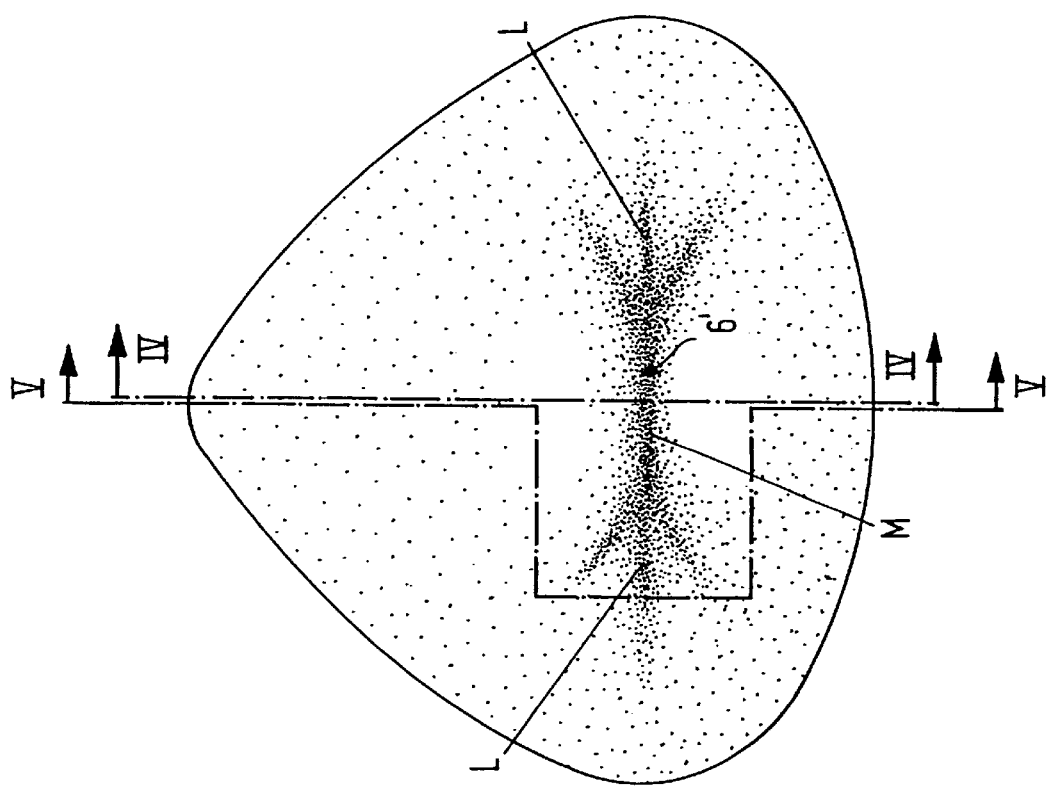
FIG. 3 a top view of the back of a breast prosthesis according to a second embodiment of the invention in the undeformed state of the prosthesis.
Figure 5:
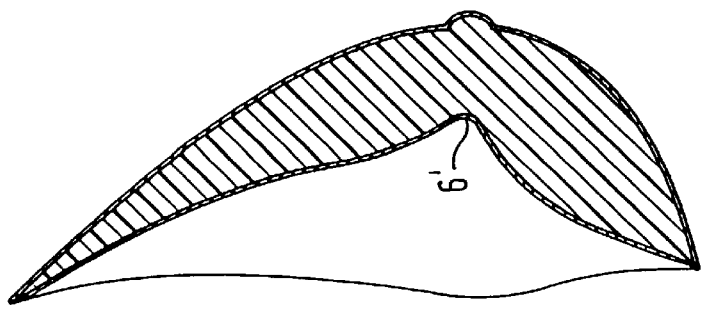
FIG. 5 a cross section through the breast prosthesis shown in FIG. 3 along line V—V in FIG. 3, as seen in the direction of the arrows, with the prosthesis in an undeformed state.

As shown in FIG. 3 in conjunction with FIGS. 4 and 5, notch 6' has a middle area M and two lateral areas L, between which the middle area M is located, as seen in the longitudinal direction of notch 6'. In the middle area M of notch 6', the opposing walls are relatively steep, so that the notch 6' is relatively narrow in the middle area M. In the two lateral areas L of the notch 6', the opposing walls are designed to be shallower than in the middle area, so that notch 6' is wider there than in the middle area M but nevertheless has the same depth as in the middle area M. In addition, in the middle area M of notch 6', the lower wall has a slight curvature to the rear for a length before it makes a definite downward change in direction. In comparison with that, the upper wall makes a definite upward change in direction at a point not far from the deepest point of notch 6'. Consequently, the area of the back side 3' which is below notch 6' is characterized by a greater bulge than the upper area of the back side 3' above the notch 6'.

When the prosthesis according to the second embodiment sags under the influence of gravity, only the opposing walls in the middle area M of notch 6' come together, whereas the walls of notch 6' in the lateral areas L come closer but do not come in contact. In the sagging state, the upper part 10' of the prosthesis presses on a reduced area in comparison with the first embodiment, said area being formed by the lower wall of the notch 6' in its middle area M. Therefore, the material in the lower part 11' of the prosthesis is pushed down and forward to a greater extent, thus resulting in a greater bulge in the middle of the prosthesis on the front side 2'.

Owing to the steeper design, the opposing walls come in contact sooner than in the first embodiment in the middle area M of notch 6'. This means that the retardation of the sagging movement with the resulting deformation of the front side 2' in the middle and lower areas begins sooner than in the first embodiment. Stretching of the prosthesis when the wearer changes from an upright position to lying down takes place the same as in the first example.

On the basis of these two embodiments, it becomes clear that the sagging of the prosthesis can be controlled in different ways through different notch designs. Depending on the choice of the notch, there is also a difference in the curvature of the lower and middle areas of the front side 2' of the prosthesis.

The softness of the silicone rubber compound is another parameter influencing the sagging and uprighting behavior of the prosthesis. Experiments with different notch shapes and different degrees of softness of the silicone rubber compound thus make it possible to easily obtain a prosthesis that can be optimally adapted to the needs of each prosthesis wearer and satisfies even the strictest requirements for natural performance even under dynamic stresses and when the wearer is standing or lying.

What is claimed is:

1. A breast prosthesis worn in a brassiere with a prosthesis body having a front side with the shape of a natural breast, a back side with a recess and a prosthesis edge which follows a closed line on which the front side and the back side each end, with the prosthesis body having a soft elastic silicone rubber compound which is enclosed without any voids in a bag consisting of elastically expandable plastic films joined tightly together along the edge of the prosthesis, characterized in that the recess has at least one elongated notch running perpendicular to the longitudinal axis of the wearer's body, bordered by opposing walls of an upper part and a lower part of the prosthesis body and a middle section which flexibly connects the upper and lower parts, making it possible for the upper part to sag under the influence of gravity relative to the lower part when the wearer is in an upright position, where sagging of the upper part causes an elastic bending deformation of the middle section and the upper part is limited by contact of at least one part of the opposing walls of the at least one elongated notch.

2. The breast prosthesis according to claim 1, wherein when the wearer changes from an upright position to a lying position, the upper part of the prosthesis body moves upward relative to the lower part, with the opposing walls of the at least one notch moving a greater distance apart, and the front side of the prosthesis body becoming flatter.

3. The breast prosthesis according to claim 1, wherein the at least one notch has a curved shape at least in an undeformed condition, forcing the opposing walls of the notch to come in contact progressively in the longitudinal direction of the notch when the upper part sags.

4. The breast prosthesis according to claim 1, wherein the notch ends at a distance from the edge of the prosthesis, as seen in the longitudinal direction.

5. The breast prosthesis according to claim 1, wherein the recess has more than one notch running perpendicular to the longitudinal axis of the wearer's body, said notches being arranged at a distance from one another based on the longitudinal axis of the wearer's body.

6. The breast prosthesis according to claim 1, wherein the notch has steeper walls in a middle area than in two lateral areas, and only the walls in the middle area of the notch come in contact with one another to limit the sagging motion.

7. The breast prosthesis according to claim 1, wherein the silicone rubber compound is adjusted to a softness with a penetration between 150 and 230×1/10 mm.

8. The breast prosthesis according to claim 1, wherein the silicone rubber consists of two addition crosslinked components whose viscosity is in the range between 500 and 2500 mPa.s.

* * * * *